(12) United States Patent
Weyl et al.

(10) Patent No.: US 8,001,827 B2
(45) Date of Patent: Aug. 23, 2011

(54) GAS SENSOR WITH SHEATH TUBE WHEREIN THE SHEATH TUBE OR THE SENSOR ELEMENT IS THERMALLY DECOUPLED FROM THE SENSOR HOUSING

(75) Inventors: Helmut Weyl, Wiesbaden (DE); Helmut Denz, Stuttgart (DE); Matthias Entenmann, Bietigheim-Bissingen (DE)

(73) Assignee: Robert Bosch GmbH, Stuttgart (DE)

( * ) Notice: Subject to any disclaimer, the term of this patent is extended or adjusted under 35 U.S.C. 154(b) by 913 days.

(21) Appl. No.: 10/569,388

(22) PCT Filed: Jun. 23, 2004

(86) PCT No.: PCT/DE2004/001315
§ 371 (c)(1),
(2), (4) Date: May 13, 2008

(87) PCT Pub. No.: WO2005/017515
PCT Pub. Date: Feb. 24, 2005

(65) Prior Publication Data
US 2008/0223110 A1 Sep. 18, 2008

(30) Foreign Application Priority Data
Aug. 18, 2003 (DE) .................................. 103 37 840

(51) Int. Cl.
*G01N 7/00* (2006.01)
(52) U.S. Cl. ...................................................... 73/23.31
(58) Field of Classification Search .................. 204/428; 73/23.32
See application file for complete search history.

(56) References Cited

U.S. PATENT DOCUMENTS

| | | | |
|---|---|---|---|
| 4,199,424 A | | 4/1980 | Teitelbaum |
| 5,012,670 A | * | 5/1991 | Kato et al. .................... 73/31.05 |
| 5,139,639 A | | 8/1992 | Holleboom |
| 2002/0000116 A1 | * | 1/2002 | Kimata et al. ............... 73/31.05 |
| 2002/0029966 A1 | * | 3/2002 | Nelson et al. ................. 204/426 |

FOREIGN PATENT DOCUMENTS

| | | |
|---|---|---|
| DE | 19608543 | 9/1997 |
| DE | 19616341 | 10/1997 |
| DE | 199 24 319 | 12/2000 |
| JP | 55-39099 | 3/1980 |
| JP | 2003 194764 | 7/2003 |

* cited by examiner

*Primary Examiner* — Hezron Williams
*Assistant Examiner* — Nathaniel Kolb
(74) *Attorney, Agent, or Firm* — Kenyon & Kenyon LLP

(57) ABSTRACT

A sensor is provided, in particular a gas sensor for determining the concentration of a gas component in a measuring gas, which has a sensor element that projects from a housing by a measuring-gas-side end section exposed to the measuring gas, and a sheath tube having gas passageways, which is placed over the measuring-gas-side end section and affixed on the housing. To prevent condensation of water vapor contained in the measuring gas in the measuring space enclosed by the housing and the sheath tube, and thus the production of water droplets that reach the hot sensor element, sheath tube and/or sensor element are/is thermally decoupled from the housing. The thermal decoupling is produced using, for instance, a flange sleeve made of a material having poor thermal conductivity, which separates the sheath tube from the housing by a flange and, via a sleeve section, is inserted in the space between the housing and the measuring-gas-side end section of the sensor element.

15 Claims, 5 Drawing Sheets

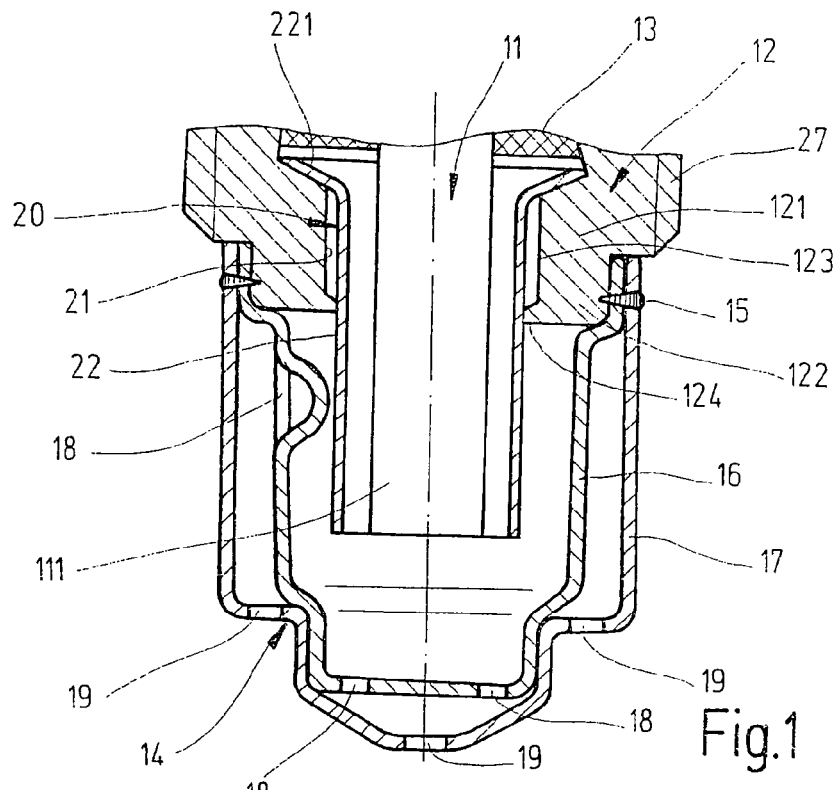
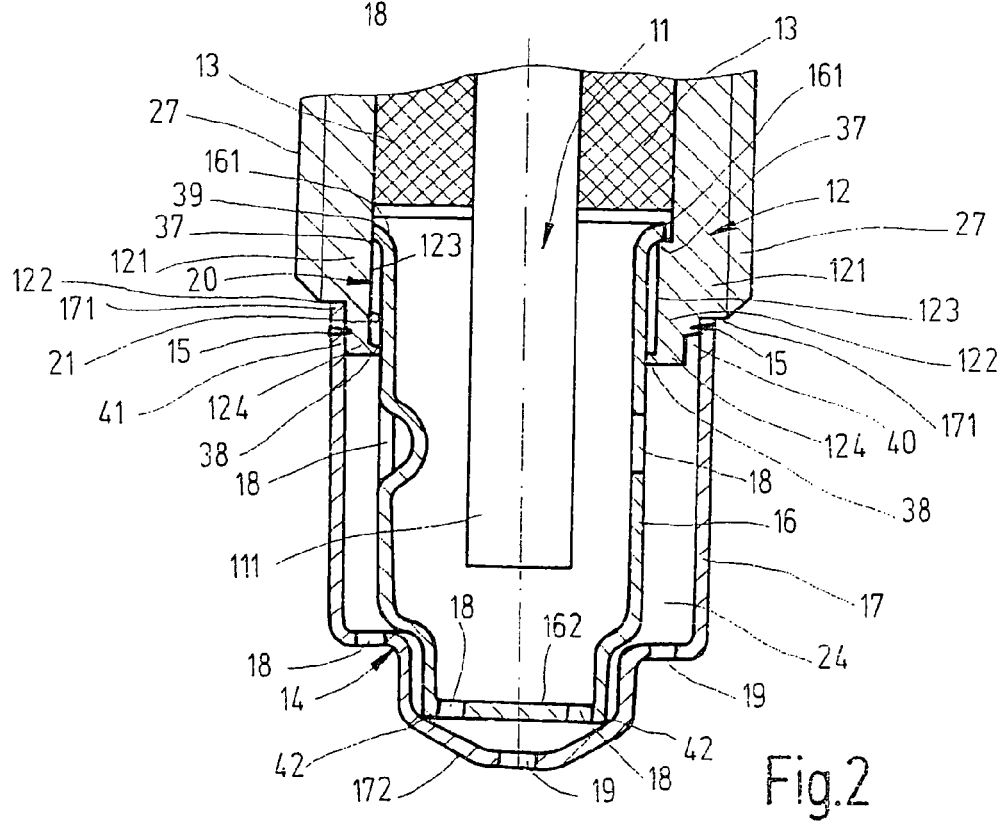

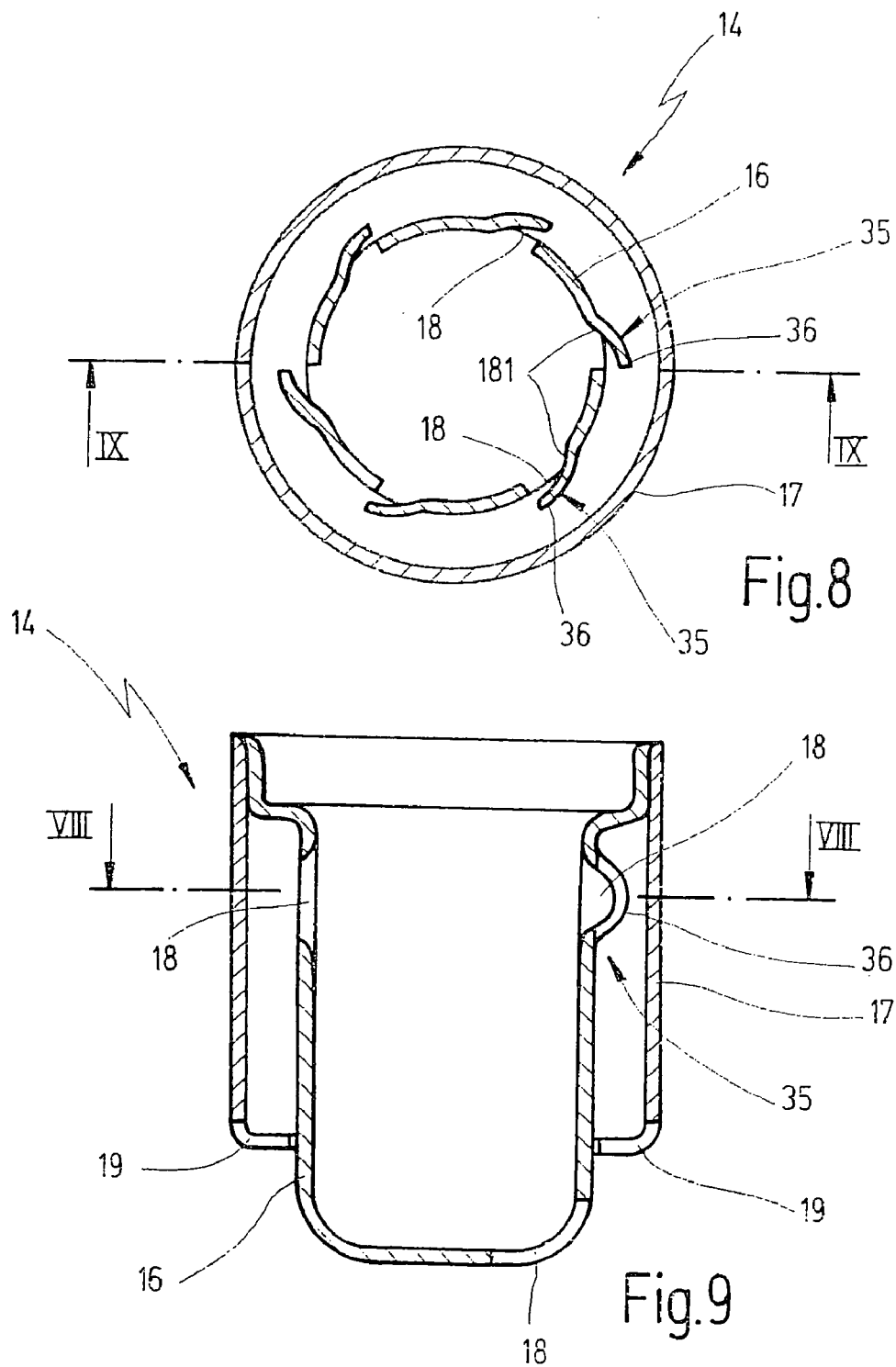

GAS SENSOR WITH SHEATH TUBE WHEREIN THE SHEATH TUBE OR THE SENSOR ELEMENT IS THERMALLY DECOUPLED FROM THE SENSOR HOUSING

FIELD OF THE INVENTION

The present invention is based on a sensor, in particular a gas sensor for determining the concentration of a gas component in a measuring gas.

BACKGROUND INFORMATION

Such sensors are used as so-called lambda sensors, for instance, to determine the oxygen concentration in the exhaust gas of an internal combustion engine. The sensor is equipped with its own electric heating device so as to bring the sensor element to its operating temperature as quickly as possible, i.e., already during the warm-up phase of the engine. The sensor element is made of ceramic materials. However, such ceramics are very sensitive to great temperature fluctuations, which lead to tears in the ceramics and thereby to malfunctions and even a total breakdown of the sensor. Extreme temperature fluctuations, also known as thermo shock, occur, for instance, during the start and in the warm-up phase of the internal combustion engine if a cold water droplet strikes the already heated sensor element. Such water droplets may form in that the water vapor produced by the engine combustion condensates on cold surfaces of the exhaust system and of the sensor during the warm-up phase, and water droplets from the condensate are entrained by the gas stream and then reach the sensor element.

In a known sensor, which is used as exhaust sensor (German Patent No. 199 24 319), a double sheath tube, which is made up of an inner and an outer tube each of which is provided with gas-entry and exit openings, protects the sensor element from the action of water droplets entrained by the exhaust flow. A flow element for the exhaust gas is positioned at least one entry opening of the inner tube and/or at least one entry opening of the outer tube, the flow element diverting the exhaust gas entering the interspace enclosed by the inner and outer tube and/or entering the inner space of the inner tube, in the direction of the individual inner surface area of the inner and/or outer tube. This retains the water on the inner surface areas, and the water eventually evaporates as a result of the temperature of the exhaust gas, which increases as the internal combustion engines heats up.

SUMMARY OF THE INVENTION

The sensor, according to the present invention has the advantage of achieving rapid heating of the sheath tube and of the interior of the sheath tube into which the sensor element projects, due to the thermal decoupling of the sensor element and/or the sheath tube from the sensor housing, which heats up only gradually during the cold start because of its large mass. This reliably prevents a condensate film from forming on the inner walls of the sensor interior covered by the sheath tube, so that the danger of water droplets forming in the interior is averted and effective countermeasures are also taken to prevent any risk to the sensor element by so-called thermo shock caused by striking water droplets. Since the formation of water droplets is prevented according to the present invention, the heating of the sensor element may now already be undertaken in the beginning phase of engine operation, i.e., from the cold start to attainment of the dew point temperature, which prevents the formation of water vapor, such heating being implementable from the beginning and at full force, so that the sensor is operative within the shortest time and the lambda control is active. At the same time, the heating time of the sensor element is thereby largely independent of the installation location and of large thermal masses situated near the installation location. The overall advantages obtained by the sensor according to the present invention, such as rapid start-up capability and resistance to thermo shock as well as a short heating time regardless of installation location and installation type, are achieved by measures that are cost-effective in terms of production engineering.

The sensor according to the present invention is advantageously able to be used as lambda sensor even in internal combustion engines where large temperature differences arise in the exhaust gas between idle and full load operation and the sensor has to be installed in the exhaust pipe in a recessed manner, away from the hot exhaust flow, in order to prevent overheating. Despite the related longer heating time of the housing after the cold start and despite the sometimes long periods where the dew-point temperature on the housing mass is not exceeded in longer idling phases and at low outside temperatures, the formation of condensation in the interior of the sensor is effectively prevented.

According to a preferred specific embodiment of the present invention, the thermal decoupling is realized with the aid of a heat-conduction barrier, which is situated between the housing on one side and the sheath tube and/or sensor element on the other side.

According to an advantageous specific embodiment of the present invention, such a heat-conduction barrier is embodied as enclosed air cushion, which covers the inner wall of the measuring-gas-side end section of the housing surrounding the sensor element with reduced radial clearance.

According to an advantageous specific embodiment of the present invention, the enclosed air cushion is realized by an axially restricted ring gap between the inner wall of the measuring-gas-side end section of the housing and a tubular insert inserted in the measuring-gas-side end section.

According to an advantageous specific embodiment of the present invention, the tubular insert is formed such that it not only covers the ring gap, but on the end side projects beyond the housing to the end of the measuring-gas-side end section of the sensor element. This tubular insert thereby provides additional protection for the sensor element from water droplets. Moreover, through heat conduction by the hot exhaust gas or by the radiant heat of the sensor element, the tubular insert is heated more rapidly, so that the dew point temperature is reached faster in the environment of the sensor element.

According to an advantageous specific embodiment of the present invention, the thermal conduction barrier is realized with the aid of a flange sleeve which is inserted into the measuring-gas-side end section of the housing on the front side and affixed in the housing. The sheath tube is then no longer affixed on the housing, but on the flange sleeve.

In an advantageous specific embodiment of the present invention, the flange sleeve is made of a material having poor thermal conductivity and has a hollow-cylindrical sleeve section, which has an outer diameter that is slightly smaller than the inner diameter of the measuring-gas-side end section of the housing; it also includes a flange which radially projects from one sleeve end and covers the front end of the measuring-gas-side end section. The sheath tube is mounted on the flange of the flange sleeve. On the one hand, this flange sleeve thermally insulates the sensor element and, on the other hand, it thermally insulates the sheath tube from the housing with its large heat-absorption capacity, so that the high heat-absorption capacity of the housing has no adverse effect on the heating time of the sensor element and sheath tube.

According to an alternative specific embodiment of the present invention, the flange sleeve has a sleeve section which has an outer diameter that is considerably smaller than the inner diameter of the measuring-gas-side end section of the housing. Here, too, the flange of the flange sleeve covers the end face of the end section of the housing. The sheath tube is affixed on the bottom side of the flange facing away from the housing. The sleeve itself is spot-welded to the housing at individual pointed forms formed on the flange and/or on the end face of the end section of the housing. This results in only very small heat-conduction bridges between housing and sheath tube, and the air space forming between the inner wall of the end section of the housing and the sleeve section of the flange sleeve assumes the function of thermally insulating the sensor element from the housing.

According to an advantageous specific embodiment of the present invention, the sheath tube is surrounded by a heat insulation zone. This measure, which is used in addition to, but also instead of, the previously described measures for thermally decoupling the housing on the one side and/or the sensor element and sheath tube on the other side, reduces the risk of a condensate film forming on the inner wall of the sheath tube even under extremely unfavorable operating conditions. This measure improves the temperature shock resistance of the sensor according to the present invention, in particular in the already previously mentioned internal combustion engines where the sensor must be installed in the exhaust pipe in a "recessed" manner for reasons of excessive temperature loading of the sensor in full-load operation. The lengthened screw-in nipple used for this purpose increases the mass of the housing and its heat-absorption capacity, so that it may take three or more minutes for the dew-point temperature to be exceeded after the cold start at low ambient temperatures. Due to the insulation coating of the sheath tube, the dew-point temperature is reached much more rapidly at the inner surface of the sheath tube, and the formation of condensate film is effectively counteracted.

According to an advantageous specific embodiment of the present invention, the heat insulation zone is realized by a casing tube which encloses the sheath tube with radial clearance and is connected to the sheath tube in a gastight manner. The annular cavity present between the sheath tube and casing tube is filled with air, but in alternative specific embodiments of the present invention it may be filled with a heat-resistant insulating material or it may be voided. Furthermore, the existing cavity may additionally be utilized to accommodate the windings of an electrical heating device so as to rapidly heat the sheath tube with the aid of external sources.

According to an advantageous specific embodiment of the present invention, the sheath tube has the form of a double sheath tube which has an inner sheath tube provided with gas passageways and an outer sheath tube, which is provided with gas passageways and concentrically surrounds the inner sheath tube. Flow elements, which are bent away from the inner sheath tube in the direction of the outer sheath tube, are assigned to the gas passageways in the inner sheath tube. In addition, the edges of the passageways are rounded in a concave manner. These measures, which are implemented in addition to, but also instead of, the previously described measures for avoiding thermo shock due to water droplets striking the sensor element, have the effect that droplets, which may still begin to form at the very beginning of the cold start and which are torn off by the gas flow, are carried away to the outside by the flow elements and do not strike the sensor element. Due to the concave design of the cutting edges of the passageways, the gas flow is advantageously guided to the sensor element from the outside, but there are no sharp tear-off edges, so that a droplet that adheres to the inner wall of the inner sheath tube and is pushed along by the gas flow, will not tear off, but instead is guided along the inner sheath tube to one of the closest gas passageways.

BRIEF DESCRIPTION OF THE DRAWINGS

FIG. 1 shows a longitudinal section of a lambda sensor according to a first exemplary embodiment, in a cut-away view.

FIG. 2 shows a longitudinal section of a lambda sensor according to a second (right half section) and a third (left half section) exemplary embodiment, in a cut-away view.

FIG. 8 shows a cross section along line VIII-VIII of FIG. 9 of a modified double sheath tube of the lambda sensor.

FIG. 9 shows a section along line IX-IX in FIG. 8.

DETAILED DESCRIPTION

Figure 3:
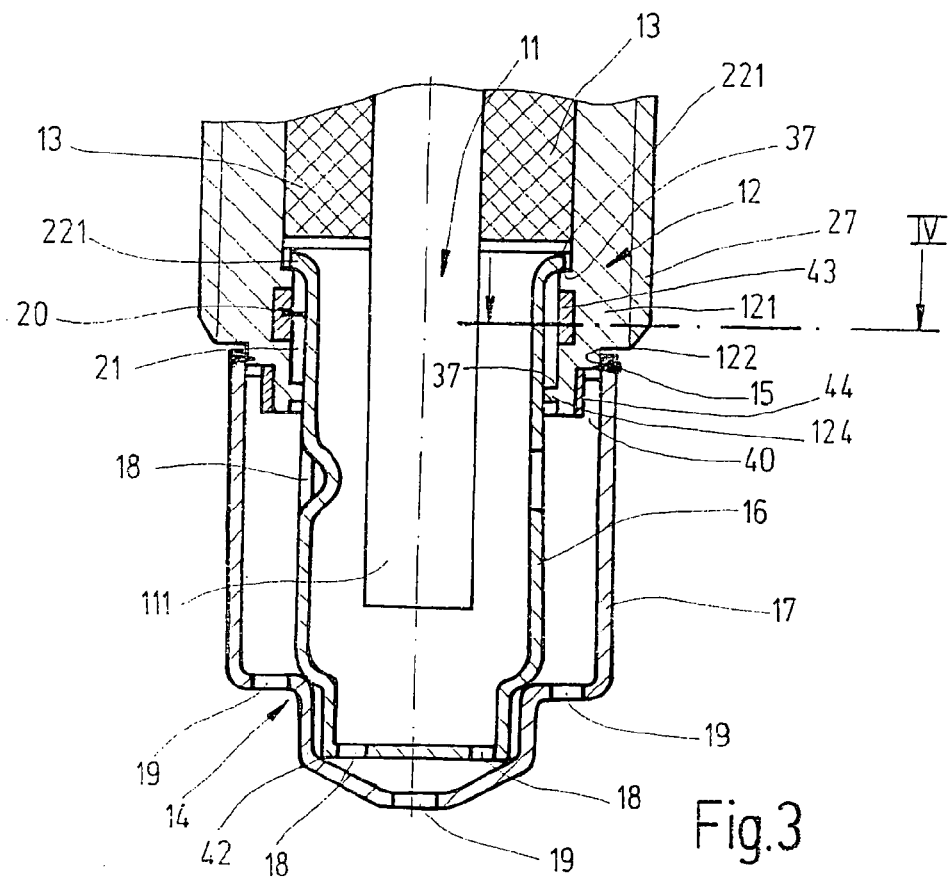
FIG. 3 shows a longitudinal section of a lambda sensor according to a fourth exemplary embodiment, in a cut-away view

The lambda sensor shown in FIG. 1 in a cut-away view in longitudinal section is used to determine the oxygen concentration in the exhaust gas of a combustion engine or an internal combustion engine. It is described as an exemplary embodiment for a general sensor used as gas sensor by which the concentration of a particular gas component in a measuring gas formed by a gas mixture is measured.

The lambda sensor has a sensor element 11, which is made of ceramic and has a measuring-gas-side end section 111 exposed to the exhaust or measuring gas, and a connection-side end section, which is not shown here, where the electric contacting of sensor element 11 for the connection to a control and evaluation device is implemented. Sensor element 11 is accommodated in a housing 12 of which only the lower measuring-gas-side end region 121 is shown in FIG. 1, where housing 12 encloses measuring-gas-side end section 111 of sensor element 11 with reduced radial clearance. Sensor element 11 is inserted in housing 12 in a gastight manner with the aid of a seal 13 and projects beyond housing 12 by measuring-gas-side end section 111. Housing 12 has a thread 27 by which the lambda sensor is screwed into a connecting piece held at an exhaust-gas pipe of the combustion engine at the installation location, in such a way that measuring-gas-side end section 111 dips into the gas flow carried in the exhaust-gas pipe. Measuring-gas-side end section 111 is enclosed by a sheath tube 14, which is slipped over a housing collar 122 formed on measuring-gas-side end region 121 of housing 12 and welded thereto in a gastight manner. The circumferential welding seam, preferably produced by laser welding, is denoted by reference numeral 15 in FIG. 1. In the exemplary embodiment of FIG. 1, sheath tube 14 is implemented in the form of a so-called double sheath tube and has a cup-shaped inner sheath tube 16 as well as a cup-shaped outer sheath tube 17, which are inserted inside each other and welded together with housing collar 122 at the cup edge. Inner sheath tube 16 and outer sheath tube 17 have been provided with gas passageways 18 and 19, respectively. A complete representation and description of the lambda sensor, which also shows the connection-side end section of sensor element 11 including electrical connection lines, can be found in DE 199 24 319 C2, for example.

To prevent condensation from forming inside sheath tube 14 and to counteract the resultant forming of water droplets that lead to a so-called temperature shock when striking the temperature-sensitive ceramic of sensor element 11, sensor element 11 is thermally decoupled from housing 12. This thermal decoupling is implemented by means of a thermal conduction barrier, which is realized by an enclosed air cushion 20 in the exemplary embodiment of FIG. 1, this air cushion covering inner wall 123 of end region 121 of housing 12. This air cushion 20 is enclosed in a ring gap 21 between inner wall 123 of measuring-gas-side end region 121 of housing 12 and a tubular insert 22 inserted in measuring-gas-side end region 121. The lower axial delimitation of ring gap 21 is formed by a radially projecting bead 124 of housing 12, while the upper axial delimitation of ring gap 21 is formed by an outwardly bent tube edge 221 of tubular insert 22. Tubular insert 22 is implemented in such a way that it projects from end region 121 of housing 12 and extends to the end of measuring-gas-side end section 111 of sensor element 11. This tubular insert 22, which projects from housing 12 and encloses measuring-gas-side end section 111 of sensor element 11 with a radial clearance, not only produces the enclosed air cushion in annular groove 21, but offers additional protection of sensor element 11 from water droplets that could perhaps enter through gas passageways 18, 19 of sheath tube 14. Moreover, tubular insert 22 is rapidly heated from the direction of the free end and contributes to the thermal insulation with respect to cold housing 12 at the air cushion.

In the exemplary embodiment of the lambda sensor shown in FIG. 2 in a part-sectional longitudinal view, sheath tube 14 is once again embodied as double sheath tube having an inner sheath tube 16 provided with gas passageways 18 and an outer sheath tube 17 provided with gas passageways 19. Both sheath tubes 16, 17 are cup-shaped; inner sheath tube 16 with its cup base 162 is supported on cup base 172 of outer sheath tube 17 via an annular, circumferential and very narrow contact surface 42. In contrast to FIG. 1, inner sheath tube 16 is inserted in the measuring-gas-side end region 121 of housing 12 and braced against its inner wall 123, while outer sheath tube 17 is slipped over end region 121 on the outside and fixedly joined to housing 12 by a circumferential welding seam 15. Inner sheath tube 16 is supported on inner wall 123 of measuring-gas-side end region 121 of housing 12 only at an upper and a lower circumferential, very narrow contact surface 37, 38, so that a ring gap 21 wish an insulating air cushion 20 enclosed therein results between inner wall 123 of measuring-gas-side end region 121 and the section of inner sheath tube 16 inserted in measuring-gas-side end region 121. Lower contact surface 38 is formed by a bead 124, which radially projects from the housing end, and upper contact surface 37 is formed by widened tube edge 161 of inner sheath tube 16. To reduce the heat transfer, circumferential contact surfaces 37, 38 may be discretized by cutouts, so that only a point-wise support of inner sheath tube 16 at inner wall 123 of housing 12 is present. In the exemplary embodiment illustrated on the right side in FIG. 2, inner sheath tube 16 is affixed in housing 12 by press fits, and in the exemplary embodiment shown on the left side of FIG. 2 it is affixed by a circumferential welding seam 39 that may also be implemented as welding points spaced apart from each other on a circumferential circle so as to reduce the heat transfer. Due to the narrow contact surfaces 37, 38 between inner sheath tube 16 and housing 12, small heat-transfer areas and minimal heat transfer result, so that in a cold start inner sheath tube 16 is able to heat up very quickly despite cold housing 12 and reaches the dew-point temperature very rapidly, thereby preventing condensation from depositing on inner sheath tube 16.

In the exemplary embodiment shown on the right side of FIG. 2, thermally conductive contact between outer sheath tube 17 and housing 12 exists only in the region of welding seam 15, at its tube edge 171. A ring gap 40 is provided between the remaining section, overlapped by outer sheath tube 17, of measuring-gas-side end region 123 of housing 12 and outer sheath tube 17. On the one hand, this ring gap 40 reduces the heat transfer area between outer sheath tube 17 and housing 12, and on the other hand it also has the effect that water droplets which may form immediately after the engine start are retained in the outer, cold region of housing 12 due to capillary effect.

In the exemplary embodiment shown in the left half of FIG. 2, a relatively large heat transfer area 41 is provided between outer sheath tube 17 and housing 12. In full load operation, this heat transfer area 41 brings about excellent cooling of outer sheath tube 17 via housing 12. Nevertheless, there is optimal thermal decoupling of inner sheath tube 16 during warm-up of the engine since the cold from housing 12 must make its way across entire outer sheath tube 17 to contact surface 42 and from there is able to transfer to inner sheath tube 16 only via a very small area. Large heat transfer area 41 therefore provides the advantage that, in the presence of extremely hot exhaust gas, the heat of outer sheath tube 17 is dissipated to cooler housing 12 via heat transfer area 41, so that only a slight heat transfer occurs from outer sheath tube 17 to inner sheath tube 16 at narrow contact surface 42. In the space between the two sheath tubes 16, 17 the hot exhaust gas is already slightly cooled by outer sheath tube 17, so that inner sheath tube 16 and sensor element 11 will no longer heat up as much. This provides an overheat protection of sensor element 11 in full loading of the engine, so that a retracted installation of the measuring sensor in the exhaust pipe will no longer be necessary.

Figure 4:
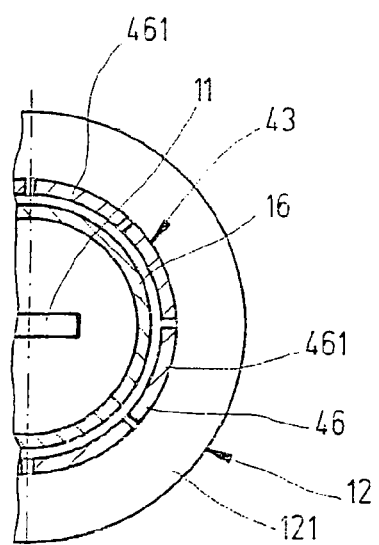
FIG. 4 shows a section along line IV-IV in FIG. 3.
Figure 5:
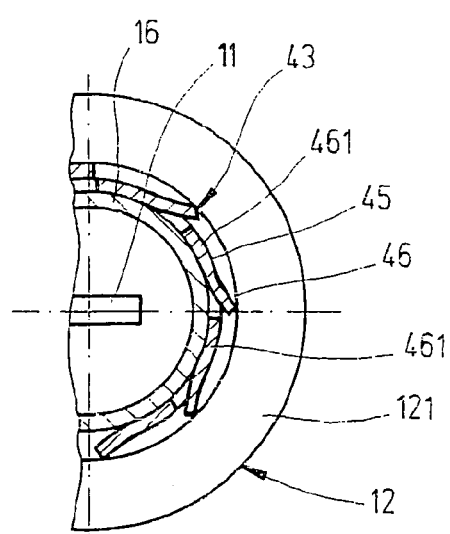
FIG. 5 shows the same representation as in FIG. 4, with a hot lambda sensor.

In the exemplary embodiment of FIGS. 3 to 5, the overheat protection, while simultaneously providing optimal thermal decoupling, is optimized during warm-up in that a variable heat transfer as a function of the temperature is provided between sheath tubes 16, 17 and housing 12. To this end, means which, with rising temperature of housing 12, produce an increasingly larger heat-conductive connection between measuring-gas-side end region 121 of housing 12 and inner and/or outer sheath tube 16, 17 are provided between measuring-gas-side end region 121 of housing 12 on the one side and inner and/or outer sheath tube 16, 17 on the other side. These means include at least one ring 43 and/or 44 which are/is held at measuring-gas-side end region 121 of housing 12. In the exemplary embodiment of FIG. 3, two rings 43 are provided, of which one ring 43 is inserted in inner wall 123 of measuring-gas-side end region 121, and other ring 44 is mounted on the outside of measuring-gas-side end region 121 of housing 12 and thus is situated in ring gap 40 between end region 121 and outer sheath tube 17. Rings 43, 44 have an identical design, so that only ring 43 will be described in the following.

As can be gathered from the sectional views of FIGS. 4 and 5, ring 43 has a cylindrical ring section 45 and a segmented ring section 46 axially abutting thereon, made from a material with a highly temperature-dependent expansion coefficient. It is possible, for instance, to use bimetals or special alloys for ring segments 461, which cause ring segments 461 to splay away from ring segment 46 with rising temperature. In FIG. 4, ring 43 is shown with a cold housing 12. Both ring sections 45, 46 are axially congruent and lie against housing 12. Inner sheath tube 16 is thermally decoupled from housing 12 and ring 43 by ring gap 21. In FIG. 5, ring 43 is shown with a warm housing 12. Ring segments 461 are bent inwardly due to the temperature increase and rest against inner sheath tube 16 via a large surface. This provides an excellent heat transfer from inner sheath tube 16 to housing 12, so that heat is dissipated from inner sheath tube 16 via housing 12 in the presence of very hot exhaust gas as is the case in full loading of the engine, and sensor element 11 is effectively protected from overheating.

The function of ring 44 is the same as that of ring 43, with the exception that the ring segments bend outwardly when heated and come to lie against a large area of outer sheath tube 17, thereby providing an excellent heat transfer between outer sheath tube 17 and housing 12.

Figure 6:
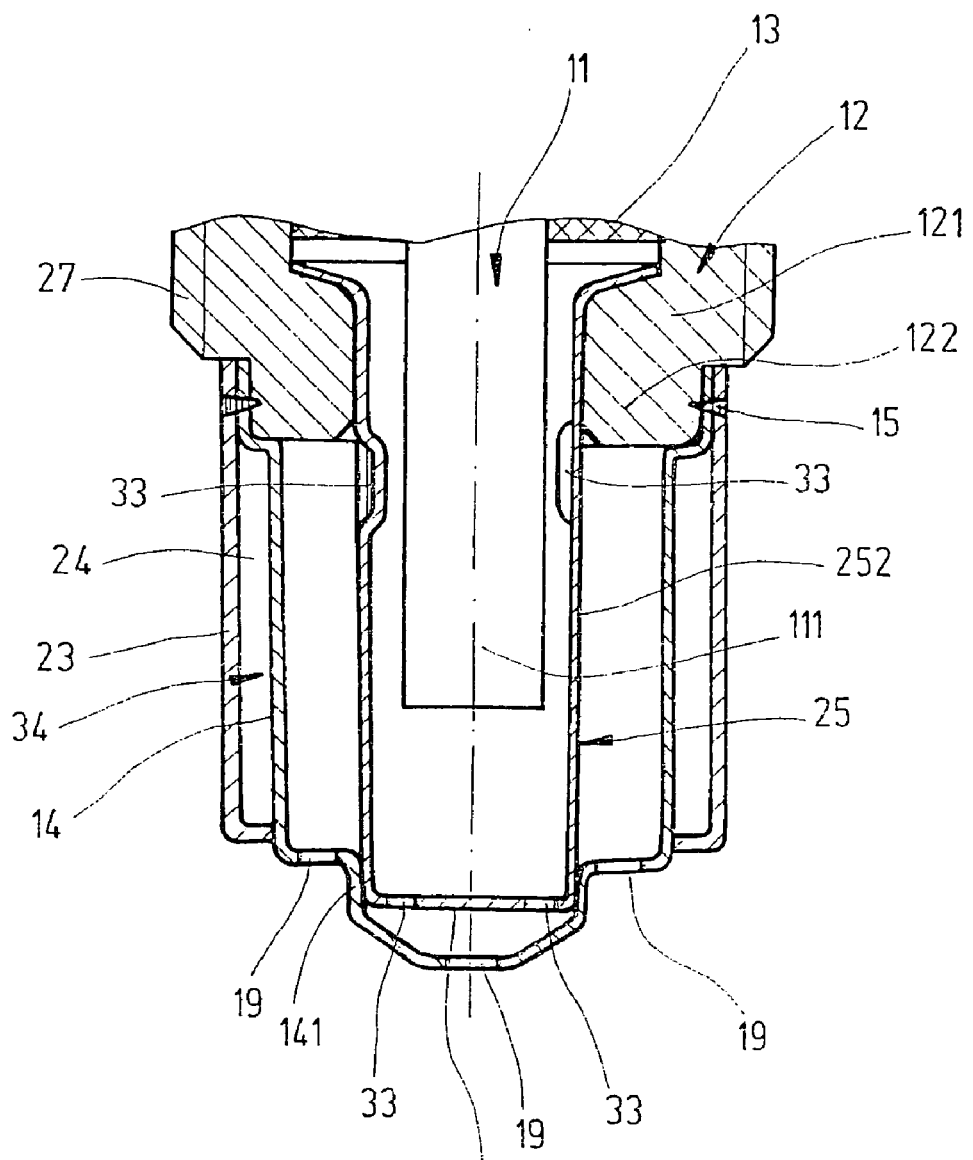
FIG. 6 shows a longitudinal section of a lambda sensor according to a fifth exemplary embodiment, in a cut-away view.

In the exemplary embodiment of the lambda sensor shown in FIG. 6 in a cutaway view, a jacketed tube 23 has been slipped over sheath tube 14, which is a single sheath tube in this case, this jacketed tube having a larger diameter than sheath tube 14 and being joined to sheath tube 14 in a gastight manner. To this end, jacketed tube 23 is welded onto housing collar 122 of housing 12 at the upper edge, together with sheath tube 14, and at the other tube end is mounted on sheath tube 14 by press fit. However, instead of the press fit, gastight welding of sheath tube 14 and jacketed tube 23 may be implemented here as well. Sheath tube 14 has the shape of a cup, like double sheath tube 14 in FIG. 1, and gas passageways 19 in cup base 141. Cavity 24 enclosed between jacketed tube 23 and sheath tube 14 forms a heat insulation zone 34, which encloses sheath tube 14. This heat insulation zone 34 in turn prevents condensation from forming on the inner wall of sheath tube 14. In order to realize the water-droplet-repelling function of double sheath tube 14 in FIG. 1 in this case as well, an inner tube 25 is inserted in measuring-gas-side end region 121 of housing 12—similar to FIG. 1—, and affixed on housing 12, the housing surrounding measuring-gas-side end section 111 of sensor element 11 with radial clearance and projecting up to cup base 141 of sheath tube 14. Cup base 141 of sheath tube 14 has the form of a basin and, at the extremity, inner tube 25 dips into the basin opening of cup base 141 of sheath tube 14. Gas passageways 19 are situated in the basin floor on the one side and at the basin edge on the other hand. In contrast to tubular insert 22 in FIG. 1, which is open at the end, inner tube 25 is in the shape of a cup and has gas passageways 33 in cup base 251 and cup wall 252 whose function corresponds to the function of gas passageways 18 in inner sheath tube 16 in FIG. 1.

Using inner tube 25, it is also possible—though not shown further—to produce the enclosed air cushion forming a heat transfer barrier, as shown in FIG. 1. To this end, it is merely required—as described in connection with FIG. 1—to provide ring gap 21, shown in FIG. 1, in the inner wall of measuring-gas-side end region 121 of housing 12.

In alternative embodiments of the lambda sensor described in connection with FIG. 6, cavity 24 existing between jacketed tube 23 and sheath tube 14 may also be voided or filled with a temperature-stable heat insulation material. In both instances, heat insulation zone 34 enclosing sheath tube 14 is produced. In a preferred specific embodiment, the radial width of hollow cavity 24 amounts to approximately 1 mm so as to achieve a very effective insulating effect, and—for reasons of stability—the wall thickness of jacketed tube 23 is greater than that of sheath tube 14, which is kept relatively thin in order to keep the heat-absorption capacity as low as possible.

Figure 7:
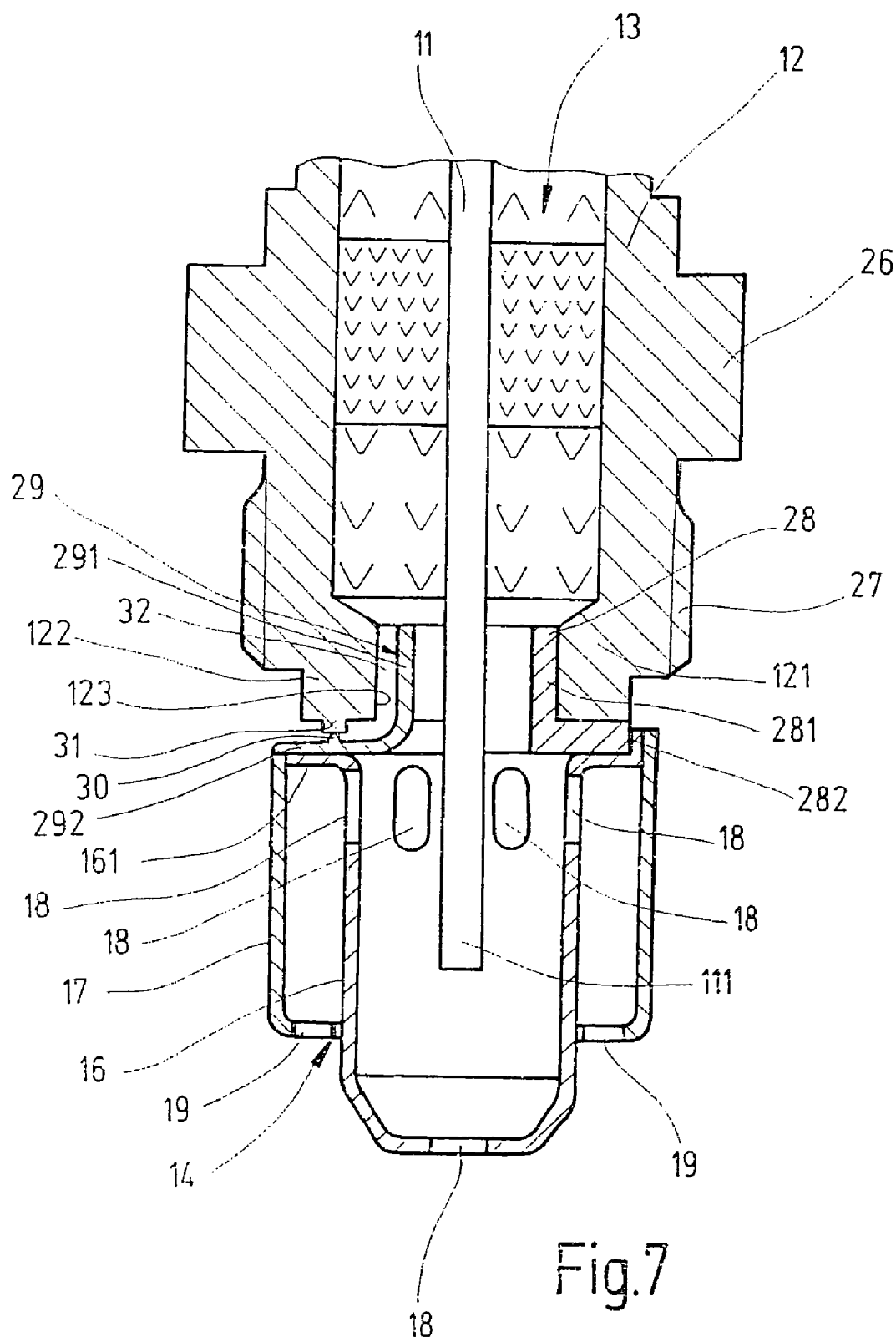
FIG. 7 shows a longitudinal section of a lambda sensor according to a sixth exemplary embodiment, in a cut-away view, with two variants of thermal decoupling (left and right half section).

The exemplary embodiment of the lambda sensor shown in FIG. 7 shows a larger cutaway portion of the lambda sensor. Illustrated is the gastight affixation of sensor element 11 in housing 12 with the aid of seal 13, as well as a hex nut 26 formed on housing 12 to screw in housing 12 at the installation location, using its thread 27. Sheath tube 14, in this case configured as double sheath tube similar to FIG. 1, is once again placed against housing 12 at the extremity, but thermally decoupled from housing 12. Two different realizations of thermal decoupling are shown in the exemplary embodiment of FIG. 3, i.e., one on the left and one on the right side of the drawing. In both cases, like in FIG. 1, the thermal decoupling is achieved by a thermal conduction barrier, which is produced by a flange sleeve 28 and 29, half of which is shown in each case in the right and left side of the drawing. Each flange sleeve 28 or 29 has a sleeve section 281 or 291, respectively, and a flange 282 and 292, respectively, which radially project from one sleeve end. Flange sleeve 28 shown on the right half of the drawing in a half-section is made of a material having poor thermal conductivity or a thermally insulating material. The outer diameter of sleeve section 281 is slightly smaller than the inner diameter of measuring-gas-side end region 121 of housing 12. The outer diameter of flange 282 is dimensioned in such a way that it completely covers the end face of measuring-gas-side end region 121 once sleeve section 281 is inserted in measuring-gas-side end region 121. Flange sleeve 28 is affixed on housing 12, and sheath tube 14 is fixedly joined to flange 282 of flange sleeve 28.

In flange sleeve 29 shown on the left side of the drawing of FIG. 7, sleeve section 291 has an outer diameter that is considerably smaller than the inner diameter of measuring-gas-side end region 121 of housing 12. The outer diameter of flange 292 has approximately the same dimensions as the outer diameter of sheath tube 14. Cup-shaped inner sheath tube 16 has a radially bent cup edge 161, which lies flat against flange 292 of flange sleeve 29 and is fixedly joined to the front end of outer sheath tube 17 at the edge end. Cup edge 161 and flange 292 are permanently joined to one another. On the surfaces of flange 292 and the end face of measuring-gas-side end region 121 of housing 12 facing one another, individual pointed forms 30 and 31, respectively, are provided, which lie on top of one another. Flange 292 and housing 12 are welded to each other at these forms 30, 31, so that only a few small heat-conducting bridges exist between housing 12 and sheath tube 14. Air space 32 present between flange sleeve 29 on the one side and inner wall 123 and the end face of measuring-gas-side end region 121 of housing 12 on the other side, forms a thermal conduction barrier, so that both sheath tube 14 and sensor element 11 are thermally decoupled from housing 12.

Sheath tube 14 shown in two different sections in FIGS. 8 and 9 and implemented as double sheath tube 14, may be used in the sensors described in connection with FIGS. 1 and 7 as an alternative to sheath tube 14, configured as double sheath tube, shown and described there. Sheath tube 14 in turn has an inner sheath tube 16, which has gas passageways 18, and an outer sheath tube 17, which has gas passageways 19 and concentrically surrounds the inner sheath tube 16. Assigned to gas passageways 18 on inner sheath tube 16 are flow elements 35, which are bent away from inner sheath tube 16 and directed toward outer sheath tube 17. Flow elements 35 are formed by bulges 36, which bulge in the direction of outer sheath tube 17. Bulges 36 have an angle of pitch with respect to the outer surface of inner sheath tube 16 such that a tangential gas flow is produced in the direction of the outer surface of inner sheath tube 16. Furthermore, cutting edges 181 of gas passageways 18 in inner sheath tube 16 are rounded in a concave manner, so that no sharp edges are created at which water droplets possibly propelled along the inner surface of inner sheath tube 16 by the gas flow may tear off from the inner surface.

What is claimed is:

1. A sensor, comprising:
a housing;
a sensor element projecting from the housing by a measuring-gas-side end section exposed to a measuring gas; and
a sheath tube including gas passageways, the sheath tube being placed over the measuring-gas-side end section and affixed on the housing, wherein at least one of the sheath tube and the sensor element is thermally decoupled from the housing by a thermal conduction barrier formed by an enclosed air cushion separated from the measuring gas,
wherein:
the thermal conduction barrier is situated between the housing on one side and the sheath tube on another side.

2. A sensor, comprising:
a housing;
a sensor element projecting from the housing by a measuring-gas-side end section exposed to a measuring gas;
a sheath tube including gas passageways, the sheath tube being placed over the measuring-gas-side end section and affixed on the housing, wherein at least one of the sheath tube and the sensor element is thermally decoupled from the housing by a thermal conduction barrier formed by an enclosed air cushion separated from the measuring gas; and
a tubular insert inserted in the measuring-gas-side end region, wherein:
the thermal conduction barrier is situated between the housing on one side and at least one of the sheath tube and the sensor element on another side
the housing includes a measuring-gas-side end region that surrounds the sensor element with a radial clearance,
the enclosed air cushion covers an inner wall of the measuring-gas-side end region,
the sensor has a longitudinal axis, and
the air cushion is enclosed in an axially restricted ring gap between the inner wall and the tubular insert.

3. The sensor as recited in claim 2, wherein:
the ring gap is restricted at a lower end by a projecting bead of the housing and at an upper end by a bent tube edge of the tubular insert.

4. The sensor as recited in claim 3, wherein:
the tubular insert projects beyond the housing up to an end of the measuring-gas-side end section of the sensor element.

5. A sensor, comprising:
a housing;
a sensor element projecting from the housing by a measuring-gas-side end section exposed to a measuring gas; and
a sheath tube including gas passageways, the sheath tube being placed over the measuring-gas-side end section and affixed on the housing, wherein at least one of the sheath tube and the sensor element is thermally decoupled from the housing by a thermal conduction barrier formed by an enclosed air cushion separated from the measuring gas,
wherein:
the thermal conduction barrier is situated between the housing on one side and at least one of the sheath tube and the sensor element on another side
the housing includes a measuring-gas-side end region that surrounds the sensor element with reduced radial clearance,
the thermal conduction barrier is produced by way of a flange sleeve that is inserted in a measuring-gas-side end region of the housing, and
the sheath tube is affixed on the flange sleeve.

6. The sensor as recited in claim 5, wherein:
the flange sleeve includes thermally insulating material and a hollow-cylindrical sleeve section having an outer diameter that is smaller than an inner diameter of the measuring-gas-side end region of the housing,
a first flange radially projects at one sleeve end of the flange sleeve and covers an end face of the measuring-gas-side end region of the housing, and
the sheath tube is permanently joined to the flange.

7. The sensor as recited in claim 5, wherein:
the flange sleeve includes a hollow-cylindrical sleeve section having an outer diameter that is substantially smaller than an inner diameter of the measuring-gas-side end region of the housing,
a flange that radially projects at one sleeve end and covers end face of the measuring-gas-side end region,
the flange is spot-welded to the housing at individual, pointed forms on at least one of the flange and at the end face of the measuring-gas-side end region of the housing and
the sheath tube is affixed on a bottom side of the flange facing away from the housing.

8. A sensor, comprising:
a housing;
a sensor element projecting from the housing by a measuring-gas-side end section exposed to a measuring gas; and
a sheath tube including gas passageways, the sheath tube being placed over the measuring-gas-side end section and affixed on the housing, wherein at least one of the sheath tube and the sensor element is thermally decoupled from the housing by a thermal conduction barrier formed by an enclosed air cushion separated from the measuring gas,
wherein:
the thermal conduction barrier is situated between the housing on one side and at least one of the sheath tube and the sensor element on another side
the housing includes a measuring-gas-side end region that surrounds the sensor element with a radial clearance,
the enclosed air cushion covers an inner wall of the measuring-gas-side end region,
the sheath tube includes a double sheath tube having an inner sheath tube provided with gas passageways and an outer sheath tube having gas passageways, and the air cushion is enclosed in an axially delimited ring gap between the inner wall of the measuring-gas-side end region of the housing and the inner sheath tube inserted in the end region.

9. The sensor as recited in claim 8, wherein:
the ring gap is delimited at a lower end by a projecting bead of the housing having a small contact surface and at an upper end by a widened tube edge of the inner sheath tube, the inner sheath tube being braced via a narrow area on the inner wall.

10. The sensor as recited in claim 9, wherein:
the outer sheath tube is disposed over the measuring-gas-side end region of the housing on the outside, and
the inner sheath tube is braced via an annular, narrow contact surface on the outer sheath tube.

11. The sensor as recited in claim 10, wherein:
via a tube edge of the outer sheath tube, the outer sheath tube is fixed in place, by welding, on the measuring-gas-side end region of the housing, and
a second ring gap is provided between a section of the end region overlapped by the outer sheath tube and the outer sheath tube.

12. The sensor as recited in claim 11, further comprising:
an arrangement, positioned between the end region on one side and at least one of the inner sheath tube and the outer sheath tube on another side, for producing a variable heat transfer between the housing and at least one of the inner sheath tube and the outer sheath tube as a function of a temperature of the housing.

13. The sensor as recited in claim 12, wherein:
the arrangement forms a heat transfer area between the housing and at least one of the inner sheath tube and the outer sheath tube that becomes larger as a temperature of the housing increases.

14. The sensor as recited in claim 13, wherein:
the arrangement includes at least one ring retained at the measuring-gas-side end region,
the at least one ring includes a cylindrical ring section and an axially abutting segmented ring section, and
ring segments of the segmented ring section are configured in such a way that they are forced apart when the segmented ring section heats up and come to lie against at least one of the inner sheath tube and the outer sheath tube.

15. The sensor as recited in claim 14, wherein:
the at least one ring includes a first ring and a second ring,
the first ring is inserted in the inner wall of the measuring-gas-side end region of the housing, and
the second ring is placed over an outer wall of the measuring-gas-side end region of the housing.

* * * * *